(12) United States Patent
Jones

(10) Patent No.: US 11,701,124 B2
(45) Date of Patent: Jul. 18, 2023

(54) TOURNIQUET DEVICE

(71) Applicant: UNIVERSITY OF CENTRAL LANCASHIRE, Preston (GB)

(72) Inventor: Martin J. Jones, Lancashire (GB)

(73) Assignee: UNIVERSITY OF CENTRAL LANCASHIRE, Preston (GB)

(*) Notice: Subject to any disclaimer, the term of this patent is extended or adjusted under 35 U.S.C. 154(b) by 320 days.

(21) Appl. No.: 16/321,158

(22) PCT Filed: Jul. 27, 2017

(86) PCT No.: PCT/GB2017/052196
§ 371 (c)(1),
(2) Date: Jan. 28, 2019

(87) PCT Pub. No.: WO2018/020255
PCT Pub. Date: Feb. 1, 2018

(65) Prior Publication Data
US 2021/0093326 A1    Apr. 1, 2021

(30) Foreign Application Priority Data

Jul. 29, 2016 (GB) ...................................... 1613131

(51) Int. Cl.
*A61B 17/132* (2006.01)
(52) U.S. Cl.
CPC ................. *A61B 17/1322* (2013.01)
(58) Field of Classification Search
CPC ..... A61B 17/12; A61B 17/122; A61B 17/132; A61B 17/1322; A61B 17/1325;
(Continued)

(56) References Cited

U.S. PATENT DOCUMENTS 1,983,969 A * 12/1934 Davis .................... A61B 17/122
606/120
RE19,924 E    4/1936 Cohen
(Continued)

FOREIGN PATENT DOCUMENTS

CN    201139818 Y    10/2008
CN    201404260 Y    2/2010
(Continued)

OTHER PUBLICATIONS

International Search Report and Written Opinion, European Patent Office, PCT/GB2017/052196, dated Dec. 19, 2017, 18 pages.
(Continued)

*Primary Examiner* — Melanie R Tyson
(74) *Attorney, Agent, or Firm* — Taft Stettinius & Hollister LLP; Stephen F. Rost

(57) ABSTRACT

A tourniquet device includes a first jaw having a first tapered tip, and a second jaw having a second tapered tip. The first and second jaws are moveable towards one another to provide a pressure to a member positioned between the jaws. The first tapered tip is offset from the second tapered tip such that the first tapered tip and the second tapered tip are moveable relative to one another in separate planes and the first tapered tip is moveable past the second tapered tip as the first and second jaws are moved towards one another.

17 Claims, 2 Drawing Sheets

(58) Field of Classification Search
CPC ...... A61B 17/1327; A61B 2017/12004; A61B 2017/12009; A61B 17/1227; A61B 17/08; A61B 17/083; A61F 2/005; A61F 2/0054
See application file for complete search history.

(56) References Cited

U.S. PATENT DOCUMENTS

| | | | | |
|---|---|---|---|---|
| 2,660,174 | A | * | 11/1953 | Franklin ............ A61B 5/0235 606/202 |
| 4,139,007 | A | * | 2/1979 | Diamond ............ A61F 2/0054 128/842 |
| D268,523 | S | | 4/1983 | Scanlan, Jr. et al. |
| 4,942,885 | A | | 7/1990 | Timmons |
| 6,138,678 | A | * | 10/2000 | Nilsson ............ A61F 2/0054 128/885 |
| 6,607,542 | B1 | * | 8/2003 | Wild ............ A61B 17/1222 606/139 |
| 2008/0262535 | A1 | | 10/2008 | Gavriely et al. |
| 2009/0198152 | A1 | * | 8/2009 | Kim ............ A61B 5/150068 600/583 |
| 2010/0274268 | A1 | | 10/2010 | Singh et al. |
| 2011/0009853 | A1 | * | 1/2011 | Bertolero ............ A61B 17/122 606/14 |
| 2012/0221041 | A1 | * | 8/2012 | Hansson ............ A61B 17/135 606/203 |

FOREIGN PATENT DOCUMENTS

| | | |
|---|---|---|
| CN | 102440817 A | 5/2012 |
| EP | 1139885 A2 | 10/2001 |
| EP | 2074954 A1 | 7/2009 |

OTHER PUBLICATIONS

U.K. Search Report, U.K. Intellectual Property Office, GB1613131.0, dated Jan. 27, 2017, 4 pages.
European Patent Office ("EPO"); EPO Notification of the Examination Report; dated Feb. 7, 2023; pp. 1-9.

* cited by examiner

TOURNIQUET DEVICE

This application is a U.S. national stage application under 35 U.S.C. § 371 of PCT International Application Serial No, PCT/GB2017/052196, which has an international filing date of Jul. 27, 2017, designates the United States of America, and claims the benefit of GB Application No. 161311.0, which was filed on Jul. 29, 2016, the disclosures of which are hereby expressly incorporated by reference in their entirety.

This invention relates to a tourniquet device, and, in particular, to a tourniquet device for providing a constrictive pressure to a limb or appendage.

BACKGROUND

Tourniquets provide a constricting or compressive force or pressure and are used to control venous and arterial circulation to an extremity for a period of time. In particular, a circumferential pressure is applied to the extremity by the tourniquet and this pressure causes the temporary occlusion of blood vessels therein.

Tourniquet application is a necessary requirement for many procedures including surgery on limbs and digits and hypospadias treatment. When using a tourniquet, restriction of the blood flow to the extremity should be controlled and be proportionate to the anatomical and/or physiological needs of the patient and any clinical requirements associated with the procedure being performed. It is known that problems can arise if the tourniquet is over-tightened or if it is left on the extremity for an overly long time period (or left on indefinitely). Whilst certain prior art arrangements seek to mitigate some of these problems, none offers an entirely satisfactory solution.

It is an object of certain embodiments of the present invention to provide an improved tourniquet device.

It is an object of certain embodiments of the present invention to provide a tourniquet device that overcomes certain disadvantages associated with the prior art.

BRIEF SUMMARY OF THE DISCLOSURE

In accordance with an aspect of the present invention there is provided a tourniquet device comprising:
 a first jaw having a first tapered tip; and
 a second jaw having a second tapered tip, the first and second jaws being moveable towards one another to provide a pressure to a member positioned between the jaws;
 wherein the first tapered tip is offset from the second tapered tip such that the first tapered tip is moveable past the second tapered tip as the first and second jaws are moved towards one another.

The surface of first tapered tip may be complementary to surface of the second complementary tip.

The tourniquet device may further comprise a tightening means arranged to provide a tightening force to an external surface of the first and second jaws to move the first and second jaws together to provide pressure to a member positioned between the jaws. In certain embodiments, the tightening means may comprise a tether that is tensionable to provide the tightening force, wherein the tether may be releasably securable in a tensioned configuration. In certain embodiments, the tether may be releasably securable in a plurality of tensioned configurations, where each tensioned configuration corresponds to a predetermined applied pressure for a member of a particular circumference. The tether may comprise a plurality of projections that provide an abutment surface for releasably securing the tether in a tensioned configuration.

The tourniquet device may further comprise a frangible component arranged to fail and cause a reduction of the pressure provided by the first and second jaws. The frangible component may comprise a frangible arm that, at least in part, extends away from one of the first jaw and the second jaw, and the tightening means provides at least a proportion of the tightening force to the external surface via the frangible component. The frangible arm may have a free end that is configured to move against the external surface in response to the tightening means providing the tightening force, where the degree of movement of the free end is proportional to the tightening force applied. The tourniquet device may further comprise a stop configured to limit movement of the free end.

Additionally or alternatively, the tourniquet device may further comprise sensing means for sensing one or more of force, pressure, or time duration. The sensing means may comprise one or more digital sensors. The tourniquet device may further comprise a controller communicably coupled to the sensing means and the frangible component, wherein the controller may cause the frangible component to fail when the sensing means senses one or more predetermined conditions.

In accordance with another aspect of the present invention, there is provided a tourniquet device comprising:
 a first jaw;
 a second jaw moveable relative to the first jaw; and
 a tightening means arranged to provide a tightening force to an external surface of the first and second jaws to move the first and second jaws together to provide pressure to a member positioned between the jaws.

In certain embodiments, the tightening means may comprise a tether that is tensionable to provide the tightening force. The tether may be releasably securable in a tensioned configuration. In certain embodiments, the tether may be releasably securable in a plurality of tensioned configurations, where each tensioned configuration corresponds to a predetermined applied pressure for a member of a particular circumference.

The tether may comprise a plurality of projections that provide an abutment surface for releasably securing the tether in a tensioned configuration.

The tourniquet device may further comprise a frangible component arranged to fail and cause a reduction of the pressure provided by the first and second jaws. The frangible component may comprise a frangible arm that, at least in part, extends away from one of the first jaw and the second jaw, and the tightening means provides at least a proportion of the tightening force to the external surface via the frangible component. The frangible arm may have a free end that is configured to move against the external surface in response to the tightening means providing the tightening force, where the degree of movement of the free end is proportional to the tightening force applied. The tourniquet device may further comprise a stop configured to limit movement of the free end.

In certain embodiments, the tourniquet device may further comprise sensing means for sensing one or more of force, pressure, or time duration. The sensing means may comprise one or more digital sensors. The tourniquet device may further comprise a controller communicably coupled to the sensing means and the frangible component, wherein the controller causes the frangible component to fail when the sensing means senses one or more predetermined conditions.

In certain embodiments, the first jaw may have a first tapered tip and the second jaw may have a second tapered tip, and wherein the first tapered tip is offset from the second tapered tip such that first tapered tip is moveable past the second tapered tip as the first and second jaws are moved towards one another. The surface of first tapered tip may be complementary to surface of the second complementary tip.

In accordance with another aspect of the present invention, there is provided a tourniquet device comprising:

a first jaw;

a second jaw moveable towards to the first jaw to provide a pressure to a member positioned between the jaws; and a frangible component arranged to fail and cause a reduction of the pressure provided by the first and second jaws.

The frangible component may be configured to break or otherwise fail when a predetermined force, pressure or time threshold is exceeded. The tourniquet device may further comprise a tightening means arranged to provide a tightening force to an external surface of the first and second jaws to move first and second jaws together to provide pressure to a member positioned between the jaws.

The frangible component may comprise a frangible arm that, at least in part, extends away from one of the first jaw and the second jaw, and the tightening means provides at least a proportion of the tightening force to the external surface via the frangible component.

The frangible arm may have a free end that is configured to move against the external surface in response to the tightening means providing the tightening force, where the degree of movement of the free end is proportional to the tightening force applied. The tourniquet device may further comprise a stop configured to limit movement of the free end.

The first jaw may have a first tapered tip and the second jaw may have a second tapered tip, and wherein the first tapered tip is offset from the second tapered tip such that first tapered tip is moveable past the second tapered tip as the first and second jaws are moved towards one another. The surface of first tapered tip may be complementary to surface of the second complementary tip.

The tourniquet device may further comprise sensing means for sensing one or more of force, pressure, or time duration. The sensing means may comprise one or more digital sensors. The tourniquet device may further comprise a controller communicably coupled to the sensing means and the frangible component, wherein the controller causes the frangible component to fail when the sensing means senses one or more predetermined conditions.

In any aspect, either or both of the first and second jaws may include a plurality of cut-outs defining a plurality of segments. In any aspect, the device may be formed as a single component. In any aspect, the device may consist of or includes a plastics material. In any aspect, an inner surface of one or both of the first jaw and second jaw may have a concave geometry.

BRIEF DESCRIPTION OF THE DRAWINGS

Embodiments of the invention are further described hereinafter with reference to the accompanying drawings, in which.

DETAILED DESCRIPTION

Figure 1:
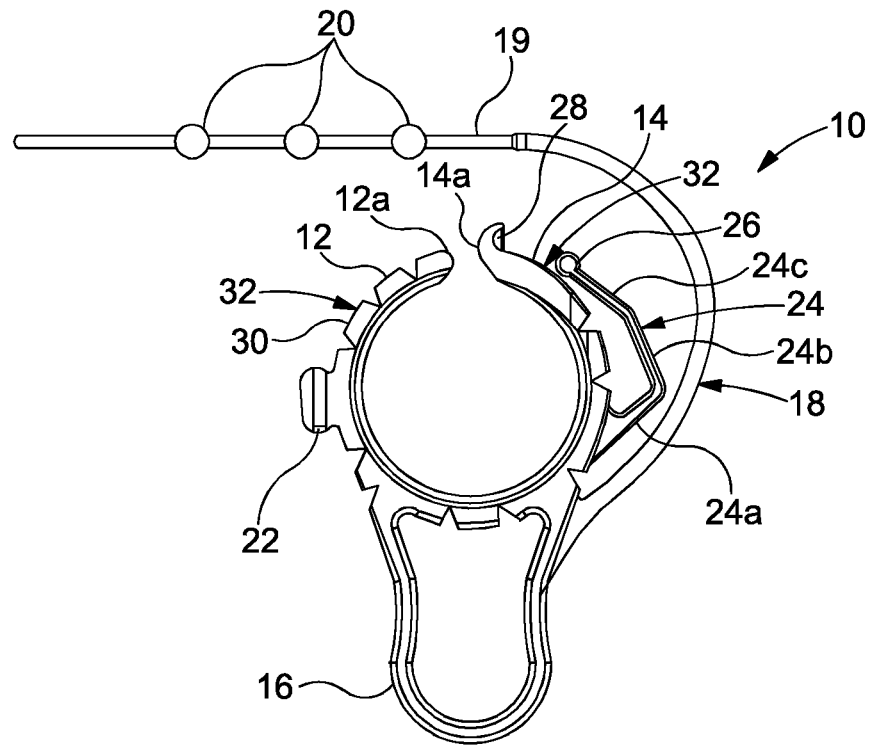
FIG. 1 is a top-down view of a tourniquet device according to an embodiment of the present invention.
Figure 4:
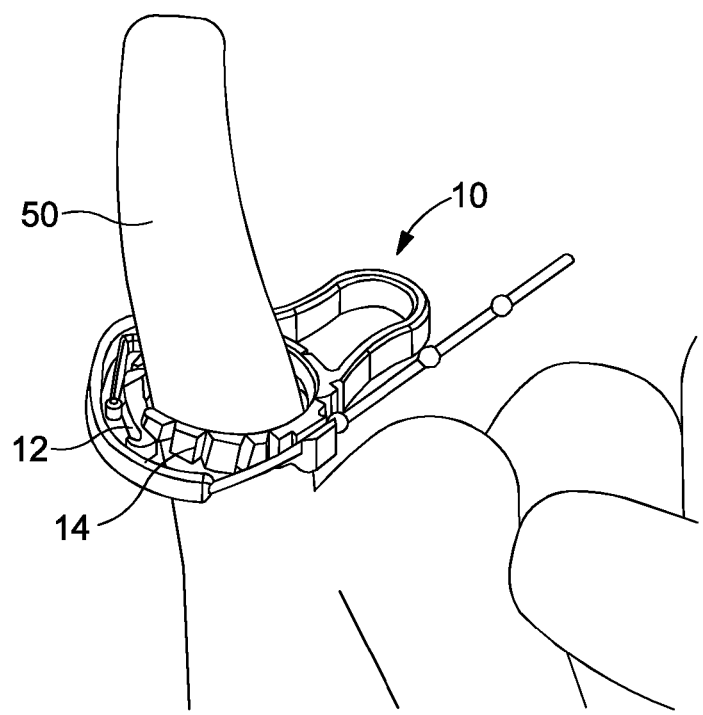
FIG. 4 shows the tourniquet device of FIG. 1 attached to an appendage of a patient.

FIG. 1 shows a top-down view of a tourniquet device 10 according to an embodiment of the invention. The tourniquet device 10 includes a first jaw 12 and a second jaw 14, where the first and second jaws 12, 14 are moveable towards one another to provide a pressure to a member 50 (see FIG. 4), such as a limb, digit or other extremity or appendage of a patient, that is positioned within the first and second jaws 12, 14. In particular, the first and second jaws 12, 14 form a generally circular open ring that may be inserted over or around a member to provide a pressure thereto. The applied pressure may cause a constriction of venous and/or arterial flow within the member. In the embodiment shown in the Figures, the first jaw 12 and the second jaw 14 each extend from one another towards a respective free end 12a, 14a. The first and second jaws 12, 14 may be flexible or otherwise biased so that they have an elastic tendency to move away from one another in the absence of any external force. Furthermore, a handle 16 is provided that is additionally connected to the first and second jaws 12, 14, and is arranged to facilitate handling of the device 10. Certain embodiments of the present invention may not include a handle, or may include a handle of a different form.

In certain embodiments, the device 10 includes a means for applying a tightening force to an external surface 32 of the first and second jaws 12, 14 so that the first and second jaws 12, 14 may move towards one another and apply a pressure to a member therebetween. In the embodiment shown in the Figures, the means for applying the tightening force to the external surface 32 comprises a tether 18 that is configured to extend around at least a portion of both of the first and second jaws 12, 14 so as to urge the first and second jaws 12, 14 towards one another. The tether 18 comprises a flexible body 19 and a series of locking protrusions 20 that are spaced from one another along the flexible body 19 and extend radially outward from the flexible body 19. The device 10 further includes a slot 22 that is sized to receive the flexible body 19 but not receive or permit the passage of the locking protrusions 20. Consequently, the tether 18 may be tensioned around the first and second jaws 12, 14 and the flexible body 19 may be received in the slot 22 so that the tether 18 is secured. Abutment between an end of the slot 22 and the locking protrusions 20 prevents inadvertent disengagement of the flexible body 19 and the slot 22, whereas intended manual disengagement may still be achieved by translating the flexible body 19 out of an open side of the slot 22. Thus, selection of the portion of the flexible body 19 that is to be received in the slot 22 will determine the extent of tensioning achieved. In certain embodiments, the spacing of the locking protrusions 20 may be designed to correspond to various predetermined ratios of member circumference to occlusion pressure. In such embodiments, securing the tether 18 with a particular locking protrusion 20 will result in a known occlusion pressure for a member of a particular circumference. In alternative embodiments, the tether 18 may be securable by means other than the locking protrusions and slot 22. Indeed, any suitable engagement mechanism may be employed. For example, any protrusion that provides an abutment surface and any feature configured to abut the abutment surface may serve as a suitable engagement mechanism.

When tensioned around the first and second jaws 12, 14, the tether 18 applies a tightening force to the external surface 32 of the first and second jaws 12, 14 that causes the first and second jaws 12, 14 to move towards one another and reduce the diameter of the circle defined by the jaws 12, 14. In doing so, the first and second jaws 12, 14 may apply a pressure to a member disposed between the jaws 12, 14.

In alternative embodiments, other means for urging the jaws 12, 14 towards one another and providing a pressure may be employed. In particular, in certain embodiments, tightening mechanisms other than a tether may be employed for applying a tightening force to an external surface of the jaws 12, 14.

In the embodiment shown in the Figures, the device 10 additionally includes a frangible arm 24 that is deformable and extends, at least in part, away from the second jaw 14. In the specific, non-limiting embodiment shown in the Figures, the frangible arm 24 is made up of multiple sections where a first section 24a extends away from the second jaw 14, a second section 24b extends from the first section 24a, and a third section 24c extends from the second section 24b towards the second jaw 14, and defines a free end of the frangible arm 24. The frangible arm 24 is flexible and is configured to break or otherwise fail under a predetermined load, or under a predetermined load over a predetermined time period. The material and formation of the frangible arm 24 may determine the load or load and time period under which the frangible arm may break or otherwise fail.

In the embodiment shown in the Figures, the frangible arm 24 is positioned so that tensioning of the tether 18 causes the frangible arm 24 to be urged against the external surface 32 of the second jaw 14. Therefore, the tightening force applied by the tether 18 on the external surface 32 is, in part, transferred via the frangible arm 24. Additionally, the frangible arm 24 maintains the tether 18 at a distance from the second jaw 14. When the tether 18 is tensioned and secured, the tightening force applied by the tether 18 results in loading of the frangible arm 24. If this loading exceeds a predetermined load (or pressure) threshold, or if it exceeds a predetermined load (or pressure) threshold for a predetermined period of time, the frangible arm 24 will fail, and consequently not maintain the tether 18 at the distance from the second jaw 14 that is was previously. As such, the second jaw 14 may move a certain distance away from the first jaw 12, thereby reducing the pressure applied by the first and second jaws 12, 14 to any member therebetween. In this manner, the frangible arm 24 may provide a fail-safe mechanism that reduces applied pressure to a member when the tightening force is undesirably high or undesirably high for an undesirably long time period.

As the frangible arm 24 is loaded, it deforms such that its free third portion 24c moves along the external surface 32 of the second jaw 14. The degree of movement may be indicative of the degree of loading, and hence indicative of the level of pressure that may be applied to a member disposed within the first and second jaws 12, 14. The external surface 32 may include reference indicia, such as a scale or a series of numbers, to indicate the degree of loading. In this sense, the frangible arm 24 serves as a mechanical "tell-tale" that may be used to monitor applied pressure.

In the embodiment shown in the Figures, the free third section 24c includes a projection 26. The projection 26 may assist in providing a visual indication of the loading of the frangible arm 24 by being more visually prominent than a free end without such a projection. Additionally, the projection 26 may abut against a stop 28 on the second jaw 14 when the projection 26 has travelled along the external surface 32 by a predetermined amount (which will be related to the degree of loading). Such abutment may inhibit or prevent further loading which may be detrimental to the member within the jaws 12, 14. Indeed, further loading may then cause the failure of the frangible arm 24 and consequently result in the reduction or release of pressure applied to the member. As shown in the Figures, the stop 28 may be curved to receive the projection 26 and reduce the likelihood of the projection 26 inadvertently moving out of and past the stop 28.

In alternative embodiments, any suitable frangible component may be employed provided that it is configured to be loaded during movement of the first and second jaws 12, 14 towards one another, and upon failure permits a reduction in the pressure applied by the first and second jaws 12, 14 to a member disposed therebetween. In embodiments where the frangible component is a frangible arm, the frangible arm may include any number of sections, and, in some embodiments, may be have a single curved section. In preferable embodiments, the reduction in pressure may be a complete release of the pressure applied to the member. In certain embodiments, the frangible component may not be associated with the second jaw 14 as described above in respect of the frangible arm 24, and instead may be associated with the first jaw 12. In certain embodiments, a plurality of frangible components may be provided (e.g. one or more associated with each of the first and second jaws 12, 14), where the plurality of frangible components may fail under different conditions from one another.

Figure 2:
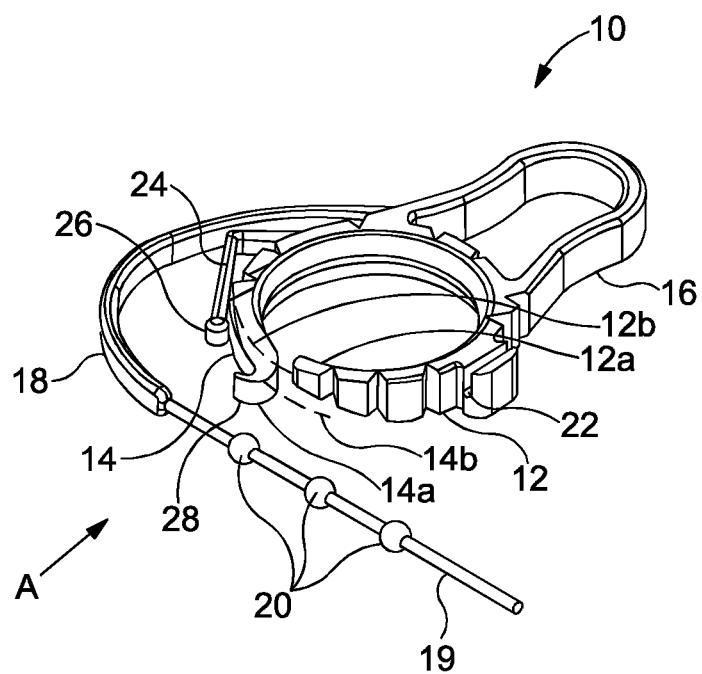
FIG. 2 is a perspective view of the tourniquet device of FIG. 1.
Figure 3:
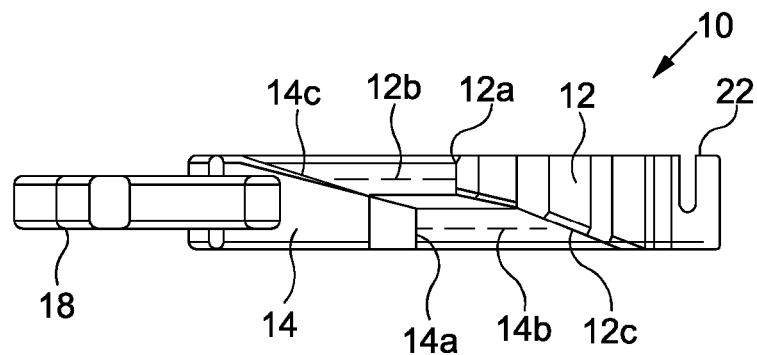
FIG. 3 is an end view of the tourniquet device of FIG. 2 as viewed along arrow A.

In the embodiment shown in the Figures, the first jaw 12 has a first tapered surface 12c such that it tapers towards its free end 12a (see FIG. 3). That is, the first jaw 12 has a first tapered tip 12a. Similarly, the second jaw 14 has a second tapered surface 14c such that it tapers towards its free end 14a and thus includes a second tapered tip 14a (see FIG. 3). The first tapered tip 12a is offset from the second tapered tip 14a such that the first tapered tip 12a is moveable past the second tapered tip 14a as the first and second jaws 12, 14 are move towards one another. FIGS. 2 and 3 show the paths that would be taken by the first tapered tip 12a and the second tapered tip 14a as the first jaw 12 and the second jaw 14 are moved towards one another. In particular, a first line 12b represents the path of the first tapered tip 12a and a second line 14b represents the path of the second tapered tip 14a. As shown in FIGS. 2 and 3, the first line 12b is offset from the second line 14b demonstrating that the first tip 12a and second tip 14a are moveable in separate planes. This arrangement may reduce the likelihood of (e.g. tissue of) the member being pinched by the jaws 12, 14 as they are tightened around (or released from) the member.

In the embodiment shown in the Figures, the first tapered surface 12c is complementary to the second tapered surface 14c such that the first tapered surface 12c contacts the second tapered surface 14c when the first jaw 12 and second jaw 14 are moved towards one another. The first and second tapered surfaces 12c,14c may slide against one another when the first jaw 12 is moved relative to the second jaw 14. Such an arrangement may further reduce the likelihood of pinching of the member during tightening or loosening of the jaws 12, 14 around the member. Additionally, the tapered profiles of the first and second jaws 12, 14 may permit the first and second jaws 12, 14 to move and accommodate a wide variety of diameters of members therebetween. That is, the first jaw 12 may overlap the second jaw 14 by a small amount when a relatively large diameter member is disposed within the jaws 12, 14, whereas the first jaw 12 may overlap the second jaw by a large amount when a relatively small diameter member is disposed within the jaws 12, 14.

In the preferable embodiment shown in the Figures, the first and second jaws 12, 14 are each formed by a series of segments that facilitate flexing and/or circumferential movement of the jaws 12, 14. In alternative embodiments, non-segmented jaws 12, 14 may be employed. In any embodiment, it is preferable that the material and/or formation of the jaws 12, 14 permits flexibility such that the jaws 12, 14 are able to move relative to one another and apply a (preferably radially inward) pressure to a member disposed therebetween.

In certain embodiments, the tourniquet device 10 may be formed as a single component (e.g. a single moulding), and such embodiments may provide a significant cost saving with regard to manufacture. Alternatively, the tourniquet device 10 may comprise an assembly of a plurality of individual components. In certain non-limiting embodiments, the tourniquet device 10 may be made of a plastics material.

Embodiments of the present invention may provide a single device 10 that offers graded proportionate uniform restriction around the girth of a limb, or extremity. The geometry of the device 10 may fit a range of differently sized members and ensure appropriate arterial and venous pressure is provided so as to achieve an appropriate occlusion relative to the proportions of the member. In certain embodiments, the device 10 reduces the risk of pinching during use. Certain embodiments of the invention permit a partially closed configuration to be adopted so as to permit exsanguination. An inner surface of the jaws 12, 14 may have a convex geometry that may extend along a portion or all of the jaws 12, 14. Such convex inner surfaces may hold an edge of the jaws 12, 14 away from a surface of the member (e.g. skin) on exsanquination. That is, a member having a circular cross section may not be contacted by the convex inner surface of the jaws 12, 14 around its entire circumference.

In certain embodiments, the device 10 has a mechanical tell-tale or a pressure sensing means mounted thereto that is responsive to pressure and/or time such that it may clearly indicate (e.g. by a visual indicator, display or alarm) over restriction/pressure application relative to the circumferential proportion of the member. The pressure sensing means may be in the form of a pressure sensor, such as a digital pressure sensor. As noted above, certain embodiments may include fail-safe means that may reduce or release pressure under certain load conditions. In certain embodiments, the pressure may be reduced or released after 15-25 minutes of a predetermined pressure or force being applied. In embodiments including sensing means, a controller may also be provided that is communicably coupled to the sensing means and the frangible components, and the controller may cause or trigger the failure of the frangible component when the sensing means determine that one or more predetermined conditions (e.g. relating to force, pressure, or time) are satisfied.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A tourniquet device comprising:
   a first jaw having a first tapered tip; and
   a second jaw having a second tapered tip, the first and second jaws being flexible and moveable towards one another to provide a pressure to a member positioned between the jaws;
   wherein the tourniquet device is a single-moulded component; and
   wherein the first tapered tip is offset from the second tapered tip such that the first tapered tip and the second tapered tip are moveable relative to one another in separate planes and the first tapered tip is moveable past the second tapered tip as the first and second jaws are moved towards one another, and
   further comprising a tightening means arranged to provide a tightening force to an external surface of the first and second jaws to move the first and second jaws together to provide pressure to the member positioned between the jaws.

2. The tourniquet device of claim 1, wherein a surface of the first tapered tip is complementary to a surface of the second tapered tip.

3. The tourniquet device of claim 1, wherein the tightening means comprises a tether that is tensionable to provide the tightening force.

4. The tourniquet device of claim 3, wherein the tether is releasably securable in a tensioned configuration.

5. The tourniquet device of claim 4, wherein the tether is releasably securable in a plurality of tensioned configurations, where each tensioned configuration corresponds to a predetermined applied pressure for a member of a particular circumference.

6. The tourniquet device of claim 4, wherein the tether comprises a plurality of projections that provide an abutment surface for releasably securing the tether in a tensioned configuration.

7. The tourniquet device of claim 1, further comprising a frangible component arranged to fail and cause a reduction of the pressure provided by the first and second jaws.

8. The tourniquet device of claim 1, further comprising a frangible component arranged to fail and cause a reduction of the pressure provided by the first and second jaws, wherein the frangible component comprises a frangible arm that, at least in part, extends away from one of the first jaw and the second jaw, and the tightening means provides at least a proportion of the tightening force to the external surface via the frangible component.

9. The tourniquet device of claim 8, wherein the frangible arm has a free end that is configured to move against the external surface in response to the tightening means providing the tightening force, where the degree of movement of the free end is proportional to the tightening force applied.

10. The tourniquet device of claim 9, further comprising a stop configured to limit movement of the free end.

11. The tourniquet device of claim 1, further comprising a sensing means for sensing one or more of force, pressure, or time duration.

12. The tourniquet device of claim 11, wherein the sensing means comprises one or more digital sensors.

13. The tourniquet device of claim 1, further comprising:
a frangible component arranged to fail and cause a reduction of the pressure provided by the first and second jaws;
a sensing means for sensing one or more of force, pressure, or time duration; and
a controller communicably coupled to the sensing means and the frangible component, wherein the controller causes the frangible component to fail when the sensing means senses one or more predetermined conditions.

14. The tourniquet device of claim 1, wherein either or both of the first and second jaws includes a plurality of cut-outs defining a plurality of segments.

15. The tourniquet device of claim 1, wherein the device consists of or includes a plastics material.

16. The tourniquet device of claim 1, wherein an inner surface of one or both of the first jaw and second jaw has a concave geometry.

17. A tourniquet device comprising:
a first jaw having a first tapered tip; and
a second jaw having a second tapered tip, the first and second jaws being flexible and moveable towards one another to provide a pressure to a member positioned between the jaws;
wherein the tourniquet device is a single-moulded component; and
wherein the first tapered tip is offset from the second tapered tip such that the first tapered tip and the second tapered tip are moveable relative to one another in separate planes and the first tapered tip is moveable past the second tapered tip as the first and second jaws are moved towards one another,
further comprising a frangible component arranged to fail and cause a reduction of the pressure provided by the first and second jaws.

* * * * *